United States Patent [19]
Barbachyn et al.

[11] Patent Number: 5,958,983
[45] Date of Patent: Sep. 28, 1999

[54] POLYAROMATIC ANTIVIRAL COMPOSITIONS

[75] Inventors: Michael R. Barbachyn; Fred L. Homa, both of Kalamazoo, Mich.; Antonio Monge, Cizur Menor, Spain; Esteban Santiago, Pamplona, Spain; Juan J. Martinez-Irujo, Pamplona, Spain; Maria Font, Pamplona, Spain

[73] Assignee: Pharmacia & Upjohn Company, Kalamazoo, Mich.

[21] Appl. No.: 09/053,177

[22] Filed: Apr. 1, 1998

Related U.S. Application Data

[60] Provisional application No. 60/043,232, Apr. 10, 1997.
[51] Int. Cl.$^6$ ........................ A61K 31/155; C07C 257/10
[52] U.S. Cl. ........................ 514/637; 514/332; 514/461; 514/585; 514/587; 514/602; 514/604; 514/631; 514/636; 514/709; 546/266; 549/487; 568/33; 564/26; 564/28; 564/83; 564/245
[58] Field of Search ........................ 514/585, 587, 514/602, 604, 636, 637, 631, 332, 461, 709; 564/26, 28, 83, 245, 246; 568/33; 546/266; 549/487

[56] References Cited

U.S. PATENT DOCUMENTS

| 5,500,322 | 3/1996 | Tanaka et al. . | |
|---|---|---|---|
| 5,679,695 | 10/1997 | Wassmundt | 514/347 |

FOREIGN PATENT DOCUMENTS

| 0 380 048 A2 | 8/1990 | European Pat. Off. . |
| 0 498 095 A1 | 8/1992 | European Pat. Off. . |
| 0519 702 | 12/1992 | European Pat. Off. . |
| 0611 754 | 8/1994 | European Pat. Off. . |
| 2290 626 | 1/1996 | United Kingdom . |
| WO82/03390 | 10/1982 | WIPO . |
| WO88/00828 | 2/1988 | WIPO . |

OTHER PUBLICATIONS

Chemical Abstracts, vol. 90, No. 2, Jan. 8, 1979.
Patent Abstracts of Japan, vol. 5, No. 184, Nov. 21, 1981.
Chemical Abstracts, vol. 126, No. 17, Apr. 28, 1997.

*Primary Examiner*—Shailendra Kumar
*Attorney, Agent, or Firm*—Lucy X. Yang

[57] ABSTRACT

The present invention relates to polyaromatic compounds having useful antiviral activity against viruses of the herpes family, to a composition containing them, and to a method of using them for the treatment of herpes viruses infections.

11 Claims, No Drawings

POLYAROMATIC ANTIVIRAL COMPOSITIONS

CROSS-REFERENCE TO RELATED APPLICATION

This application claims the benefit of the following provisional application: U.S. Ser. No. 60/043,232, filed 10 Apr. 1997, under 35 USC 119(e)(i).

FIELD OF THE INVENTION

The present invention relates to polyaromatic compounds having useful antiviral activity against viruses of the herpes family, to a composition containing them, and to a method of using them for the treatment of herpes viral infections.

BACKGROUND OF THE INVENTION

Viruses are made of nucleic acid (DNA or RNA) enclosed in a protein coat and sometimes further wrapped in a membranous envelope. Viruses are obligate intracellular parasites; they can only reproduce within a host cell. An isolated virus is unable to replicate itself, or do anything else for that matter, except infect an appropriate host cell. Of the DNA viruses, the herpes family is the source of the most common viral illnesses in man. The group consists of herpes simplex viruses type-1 and type-2 (HSV-1 and HSV-2), varicella zoster virus (VZV), cytomegalovirus (CMV), and Epstein-Barr virus (EBV). We have discovered that certain polyaromatic compounds characterized by formulas I, II, and III have potent antiviral activity against the herpes family, particularly against herpes simplex viruses. These compounds inhibit the origin-specific DNA-binding protein, an essential herpes virus replication protein, binding to the origin of viral DNA replication. As such, the compounds inhibit the initiation of herpes viral DNA synthesis in the host cell. Because of this unique mechanism, the compounds not only exhibit potent activity against herpes viruses but also are active against viral strains resistant to currently available therapeutic agents.

INFORMATION DISCLOSURE

European Patent Application 0,611,754 A1 discloses derivatives of dimerized thiourea having the structure:

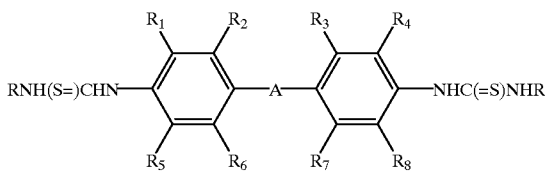

wherein

A is, among others, $CH_2$, S, O, or $SO_2$;

R is, among others, a substituted or unsubstituted aryl group having 6 to 30 carbon;

$R_1$, $R_2$, $R_3$, $R_4$, $R_5$, $R_6$, $R_7$, and $R_8$ are the same and different and are $C_{1-6}$ alkyl, $NO_2$, CN, H or halogen. The compounds are disclosed as being useful to prepare a near infrared resin material.

UK Patent Application GB 2,290,626 discloses, among others, bisurea compound of the structure:

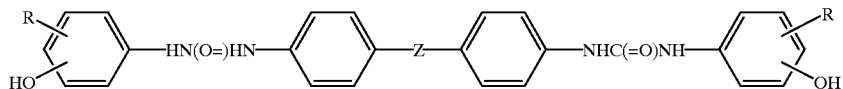

wherein

Z is $CH_2$, O, $SO_2$ or NH;

R is H, halogen, $NO_2$, $C_{1-12}$ alkyl, $C_{1-6}$ haloalkyl or $C_{1-6}$ alkoxy. Such compounds are described as being useful to prepare a thermal recording material.

U.S. Pat. No. 5,500,322 discloses, among others, a developer additive having the structure:

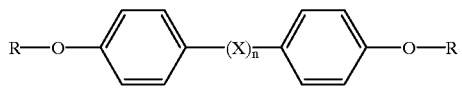

wherein

X is, among others, S, $SO_2$, O or $CH_2$;

R is an alkyl group, an alkenyl group or an arylalkyl group. Such compounds are described as being used in a toner composition.

European Patent Application 0,519,702 A1 discloses, among others, compound of the structure:

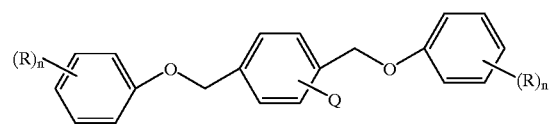

wherein

Q is H, halogen, nitro, $C_{1-6}$ alkyl, $C_{1-6}$ perhaloalkyl, $C_{1-6}$ alkylthio or $C_{1-6}$ alkyl sulfonyl;

R is, among others, $C_{1-10}$ alkyl, alkoxy, or halogen;

n is one to three. Such compounds are described as being active against picornaviruses including enteroviruses and rhinoviruses.

SUMMARY OF THE INVENTION

In one aspect, the present invention provides a compound of formula I and formula II or pharmaceutically acceptable salts thereof having useful antiviral activity against viruses of the herpes family

I

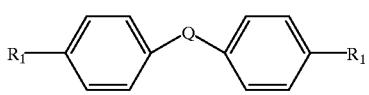

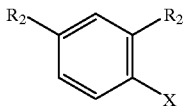

wherein:

Q is O, or $CH_2$;

$R_1$ is (a) —N=C($SCH_3$)(NH-phenyl), (b) —N=C($SCH_3$)($NHCH_2CH_2$-phenyl), (c) —N=C($SCH_3$)(NH-4-nitrophenyl), (d) —N=C($SCH_2CH_3$)($NHCH_2CH_2$-phenyl), (e) —$SO_2$NH(3-methoxyphenyl), (f) —$SO_2$NH(3-methylphenyl), or (g) —N=C($NH_2$)(phenyl); with the provisos that where Q is O, $R_1$ and $R_2$ are other than (g), and where Q is $CH_2$, $R_1$ and $R_2$ are other than (a)—(f);

$R_2$ is

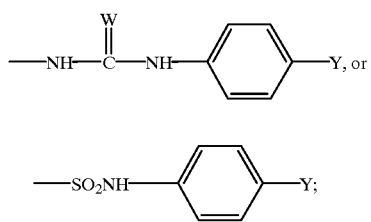

W is O, or S;
X is H, $CH_3$, $OCH_3$;
Y is $CH_3$, Cl, and $NO_2$.

In another aspect, the present invention provides a method for treating herpes viral infections which comprises an effective amount of a compound of formula II or formula III, wherein formula II is the same as defined above and formula III having the structure:

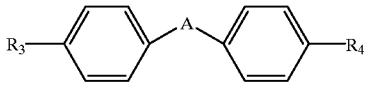

wherein A is O, $CH_2$, or S(=O)$_2$;

$R_3$ and $R_4$ are the same and are (a) —N=C($SCH_3$)(NH-phenyl), (b) —N=C($SCH_3$)($NHCH_2CH_2$-phenyl), (c) —N=C($SCH_3$)(NH-4-nitrophenyl), (d) —N=C($SCH_2CH_3$)($NHCH_2CH_2$-phenyl), (e) —$SO_2$NH(3-methoxyphenyl), (f) —$SO_2$NH(3-methylphenyl), (g) —N=C($NH_2$)(phenyl), (h) —NHC(=O)(2-furyl), (i) —NHC(=S)$NHCH_2CH_2$-phenyl, (j) —NHC(=S)NH(4-nitrophenyl), (k) —$OCH_2$(4-bromophenyl), (l) —$OCH_2$(4-chlorophenyl), (m) —$OCH_2$(4-fluorophenyl), (n) —$OCH_2$(4-pyridyl), or $R_3$ and $R_4$ are different and are (o) —OH, (p) —$OCH_2$(4-chlorophenyl), (q) —$OCH_2$(4-nitrophenyl); with the provisos that where A is —O—, $R_3$ and $R_4$ are other than (k)–(q), where A is —$CH_2$—, $R_3$ and $R_4$ are (g) or (j), and where A is S(=O)$_2$, $R_3$ and $R_4$ are other than (a)–(j).

In still another aspect, the present invention provides a pharmaceutical composition for treating herpes viral infections which comprises an effective amount of a compound of formula II or III and a pharmaceutically acceptable carrier.

The compounds of formulas I, II and III include a) Dimethyl N,N"-(oxydi-4,1-phenylene)bis [N'-(phenyl)carbamimidothioate], b) Dimethyl N,N"-(oxydi-4,1-phenylene)bis [N'-(2-phenylethyl) carbamimidothioate], c) Dimethyl N,N"-(oxydi-4,1-phenylene)bis [N'-(4-nitrophenyl) carbamimidothioate], d) Diethyl N,N"-(oxydi-4,1-phenylene)bis [N'-(2-phenylethyl)carbamimidothioate], e) Bis [N-(3-methoxyphenyl)aminosulfonyl](oxydi-4,1-phenylene), f) Bis [N-(3-methylphenyl)aminosulfonyl](oxydi-4,1-phenylene), g) N,N"-(Methylenedi-4,1-phenylene)bis [benzenecarboximidamide], h) N,N"-(4-Methoxy-1,3-phenylene)bis [N'-(4-nitrophenyl) urea], i) N,N"-(4-Methoxy-1,3-phenylene)bis [N'-(4-chlorophenyl)urea], j) N,N"-(4-Methoxy-1,3-phenylene)bis [N'-(p-tolyl)urea], k) N,N"-(4-Methyl-1,3-phenylene)bis[N'-(4-chlorophenyl) thiourea], l) N,N"-(4-Methoxy-1,3-phenylene)bis[N'-(4-chlorophenyl) thiourea], m) N,N"-(4-Methoxy-1,3-phenylene)bis[N'-(4-nitrophenyl) thiourea], n) N,N"-(1,3-Phenylene)bis[N-(p-tolyl)aminosulfonyl], o) N,N"-(Oxydi-4,1-phenylene)bis(2-furancarboxamide), p) N,N"-(Oxydi-4,1-phenylene)bis [N'-(2-phenylethyl) thiourea], q) N,N"-(Oxydi-4,1-phenylene)bis[N'-(4-nitrophenyl) thiourea], r) N,N"-(Methylenedi-4,1-phenylene)bis[N'-(4-nitrophenyl) thiourea], s) Bis(4-bromobenzyloxy)(sulfonyldi-4,1-phenylene), t) Bis(4-chlorobenzyloxy)(sulfonyldi-4,1-phenylene), u) Bis(4-fluorobenzyloxy)(sulfonyldi-4,1-phenylene), v) Bis[(4-pyridyl)methoxy](sulfonyldi-4,1-phenylene), w) (4-Chlorobenzyloxy)hydroxy(sulfonyldi-4,1-phenylene), and x) Hydroxy(4-nitrobenzyloxy)(sulfonyldi-4,1-phenylene).

DETAILED DESCRIPTION OF THE INVENTION

The present invention relates to polyaromatic compounds, their compositions and their use in medical therapy for the treatment of herpes viral infections including herpes simplex viruses type-1 and type-2 (HSV-1 and HSV-2), varicella zoster virus (VZV), cytomegalovirus (CMV), and Epstein-Barr virus (EBV). The compounds of the present invention are topically administered to the surface lesion caused by the herpes viruses.

Herpes viruses infections are recurrent infections characterized by the appearance on the skin or mucous membranes of multiple clusters of small vesicles, filled with clear fluid on slightly raised inflammatory bases. The present invention can also be applied prophylactically to prevent further recurrences of the viral lesions.

Patients of the present invention are chosen from those having been diagnosed with primary or recurrent herpes simplex type 1 or 2, herpes zoster, genital warts, chickenpox, or herpes keratitis. Such diseases and conditions are well known and readily diagnosed by physician of ordinary skill.

Topical administration means the direct contact of the active agents with the surface lesion such as, for example, by drops, sprays, ointments, lotions, creams or soaps.

The active compound or its composition is applied 1 to 5 times daily until the sore, lesion, and accompanying discomfort abates and essentially disappears.

The pharmaceutical compositions of this invention may be prepared by employing conventional technique to combine the compounds of formula II or III of this invention with a pharmaceutically acceptable carrier, and optionally, with pharmaceutically acceptable adjuvants and excipients employing standard and conventional techniques. The topical formulations may also desirably include a material which enhances absorption or penetration of the compounds of formula II or III through the skin or other affected areas.

The pharmaceutically acceptable carrier refers to any compatible non-toxic material suited for mixing with the active compounds of the present invention.

The quantity of active component, compounds of formula II or III, in a pharmaceutical composition may be varied or adjusted widely depending upon the requirements of the patient, the severity of viral infections, the potency of the particular compound being used, the particular formulation and the desired concentration. Generally, the quantity of active component will range between 0.05% to 25% by weight of the composition, preferably between 0.1% to 10% by weight of the composition.

For infections of the external tissues, e.g., mouth, eyes and skin, the formulations are preferably applied as a topical ointment or cream containing the active ingredient in an amount of, for example, 0.05 to 25% by weight of composition, preferably 0.1 to 10% w/w. When formulated in an ointment, the active ingredients may be employed with either a paraffinic or a water-miscible ointment base. Alternatively, the active ingredients may be formulated in a cream with an oil-in-water cream base.

Formulations suitable for topical administration in the eyes include eye drops wherein a compound of formula II or III is dissolved or suspended in a suitable carrier, especially an aqueous solvent. The active ingredient is preferably present in such formulations in a concentration of 0.05 to 25%, advantageously 0.5 to 10%.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

The term "pharmaceutically acceptable salts" refers to salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

Compounds of the formulas II and III of the present invention are evaluated in an assay to measure the inhibition of HSV-1 viral replication in the presence of drug over a 14–16 hour period. The assay is discussed in detail by Pritchard, M. N. et al. "A Microliter Virus Yield Reduction Assay for the Evaluation of Antiviral Compounds Against Human Cytomegalovirus and Herpes Simplex Virus", *J. Virol. Meth.*, Vol. 28, pp 101–106 (1990). Briefly, 80% confluent monolayers of Vero cells in 24 well plates are infected with low multiplicities of HSV-1 (MOI=0.001). After an absorption period of 1 hour at 37° C., the monolayers are rinsed with culture media and aliquots of compounds diluted into tissue culture media are added for 14–16 hours at 37° C. in a $CO_2$ atmosphere. The growth media is removed and 1 ml of fresh media is added to each well and plates are placed at −70° C. After a 1–5 day storage period the plates are rapidly thawed, samples are collected on ice and titrated on fresh Vero cell monolayers. Viral plaques are stained with 0.1% crystal violet in 20% alcohol for 10 minutes and are counted. Data are calculated to reflect the percentage of inhibition at indicated concentration relative to infected, non-drug treated controls.

Compounds of the formulas II and III of the present invention are also evaluated in substantially the same assay as described above to measure the inhibition of HSV-2 viral replication.

Antiviral activity against VZV are evaluated in an assay to measure the reduction of viral replication in the number viral plaques formed over five days of incubation in the presence of compounds of the present invention. Aliquots of VZV are added for 90 minutes to 24 well plates having HFF cells at 80% confluence to yield approximately 25 plaques for media treated wells. The plates are flicked and dilutions of compounds in tissue culture media at 2 time strength are added (0.5 ml per well). Immediately following the addition of drug 0.5 ml of 1.0% agarose is added to the wells and the plates are gently tapped to aid mixing. This final concentration of agarose (0.5%) is insufficient to solidify at 37° C. and serves as a semi solid overlay medium. Plates are undisturbed for five days. On day 5 the plates are examined microscopically for toxicity and plaques are counted using low power microscopy.

In the Tables, the sign "+++" refers to >90% inhibition at the indicated concentration. The sign "++" refers to >50% inhibition at the indicated concentration. The sign "+" refers to <50% inhibition at the indicated concentration. The sign "−" refers that no inhibitory activity is observed at the indicated concentration. A blank cell means the datum is not available.

Table 1 lists the corresponding level of inhibition against HSV-1 replication.

Table 2 lists the corresponding level of inhibition against HSV-2 replication.

Table 3 lists the corresponding level of inhibition against VZV replication.

TABLE 1

| % Inhibition Against HSV-1 Viral Replication | | |
|---|---|---|
| Example No. | 30 μm | 5 μm |
| 1 | + | − |
| 2 | ++ | − |
| 3 | + | + |
| 4 | + | + |
| 5 | + | − |
| 6 | + | − |
| 7 | + | − |
| 8 | + | − |
| 9 | +++ | + |
| 10 | ++ | + |
| 11 | ++ | − |
| 12 | +++ | ++ |
| 13 | +++ | + |
| 14 | + | − |
| 15 | + | + |
| 16 | ++ | + |
| 17 | ++ | + |
| 18 | ++ | + |
| 19 | + | + |
| 20 | ++ | + |
| 21 | ++ | − |
| 22 | ++ | − |
| 23 | +++ | − |

TABLE 2

% Inhibition Against HSV-2 Viral Replication

| Example No. | 10 μm | 1 μm |
|---|---|---|
| 12 | ++ | + |
| 13 | +++ | + |
| 15 | + | + |
| 17 | ++ | ++ |

TABLE 3

% Inhibition Against VZV Viral Replication

| Example No. | 10 μm | 2 μm |
|---|---|---|
| 12 | | +++ |
| 13 | | + |
| 15 | | +++ |
| 17 | | ++ |
| 18 | +++ | |
| 23 | + | |

The compounds of the present invention may be prepared by the synthetic procedures illustrated in SCHEMEs 1–3.

As shown in SCHEME 1A, diamine 1 or 2, (when necessary it can be generated from the corresponding acid addition salt by treatment in situ with triethylamine) can be reacted with two equivalents of an appropriate isocyanate or isothiocyanate wherein R is $R_1$, $R_2$, $R_3$, or $R_4$ and is as defined above; X is as defined above. The reaction occurs in a suitable solvent system, such as anhydrous dioxane, at room temperature to generate the bisurea (Y=O) or bisthiourea (Y=S) derivatives 3 or 4, respectively.

The bisthiourea derivatives (Y=S) can be alkylated with a suitable alkylating agent, for example iodomethane, in an appropriate solvent such as ethanol, and at ambient temperature to reflux temperature to generate the dimethyl carbamimidothioates 5 or 6, respectively.

As shown in SCHEME 1B, diamine 1 or 2 may also be reacted with imidates in a suitable solvent such as dioxane in the presence of acetic acid and sodium acetate at ambient temperature to generate the carboximidamides 7 or 8, respectively.

As shown in SCHEME 1C, the diamine 1 or 2 are also amenable to acylation with various acyl halide in the presence of a suitable base such as triethylamine and in an appropriate solvent, for example dichloromethane, at ambient temperature to give the corresponding bisamide 9 or 10.

The sulfonyl chlorides, 11 and 12 shown in SCHEME 2, are known compounds. Reaction of 11 or 12 with a suitable amine in the presence of an appropriate base such as pyridine and in a solvent such as dichloromethane at ambient temperature affords the corresponding sulfonamide derivatives 13 or 14, respectively.

As shown in SCHEME 3, bis-hydroxyphenyl 15 is readily alkylated with an appropriate arylhalomethanes in the presence of a suitable base, such as potassium hydroxide, and in an appropriate solvent such as dimethyl sulfoxide at ambient temperature to generate the derivatives 17. Alternatively, bis-hydroxyphenyl 15 is monoalkylated with an appropriate arylhalomethane in the presence of a suitable base, such as triethylamine, and in an appropriate solvent such as dry dioxane at reflux temperature to generate the derivatives 16.

The followings are the examples for the preparation, which is intended as an illustration of and not a limitation upon the scope of the invention.

EXAMPLE 1

Preparation of N,N"-(4-methyl-1,3-phenylene)bis[N'-(4-chlorophenyl)thiourea].

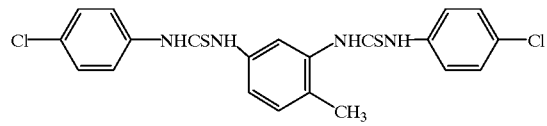

A solution of 4-chlorophenylisothiocyanate (1.39 g, 8.20 mmol) in dry dioxane (20 mL) is added dropwise, under nitrogen atmosphere, to a solution of 2,4-diaminotoluene (0.5 g, 4.10 mmol) in dry dioxane (20 mL). After 72 hours of stirring at room temperature the mixture is heated to 80° C. for 6 hours, and the solvent is eliminated under reduced pressure. The oily residue obtained is stirred with IsprOH (25 mL) for 4 hours. The white solid that precipitates is filtered and washed with n-hexane (3×25 mL) and ethyl ether (3×25 mL). The title compound is obtained as white powder. mp: 93–95° C.

$^1$H-NMR (DMSO-$d_6$, 200 MHz) δ: 2.29; 7.15–7.25; 7.34; 7.47; 9.55; 9.61; 9.67; 9.93.

IR: 1580 cm$^{-1}$.

MS-DIP (70 eV) m/z: 291.00; 168.95; 127.00.

ANAL: ($C_{21}H_{18}Cl_2N_4S_2$) C: Calcd, 54.66; Found, 54.41. H: Calcd, 3.90; Found, 3.92. N: Calcd, 12.14; Found, 11.85.

EXAMPLE 2

Preparation of N,N"-(4-methoxy-1,3-phenylene)bis[N'-(4-chlorophenyl)urea].

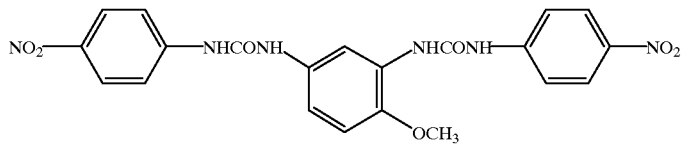

A solution of 4-nitrophenylisocyanate (1.39 g, 8.47 mmol) in dry dioxane (20 mL) is added dropwise, under $N_2$ atmosphere and with constant magnetic stirring, to a solution of 4-methoxy-m-phenylendiaminesulfate hydrate (1.00 g, 4.23 mmol) in dry dioxane (25 mL) and in the presence of triethylamine (1.2 mL). After 100 hours of stirring at room temperature, a precipitate appears. This precipitate is filtered and washed with $H_2O$ (5×25 mL). The resulting solid is suspended in IsprOH (30 mL) and stirred at room temperature for 7 hours. It is filtered and washed successively with n-hexane (3×50 mL) and ethyl ether (3×50 mL). It is then dried. The title compound is obtained as yellow hygroscopic powder. mp: 180–82° C.

$^1$H-NMR (DMSO-d$_6$, 200 MHz) δ: 3.86; 6.99–7.19; 7.69; 8.23; 8.46; 8.87; 9.27; 10.05.

IR: 1686 cm$^{-1}$.

ANAL: (C$_{21}$H$_{18}$N$_6$O$_7$. ¾ H$_2$O) C: Calcd, 52.55; Found, 52.34 H: Calcd, 4.07 Found, 4.21. N: Calcd, 17.52; Found, 17.32.

EXAMPLE 3

Preparation of N,N''-(4-methoxy-1,3-phenylene)bis [N'-(4-chlorophenyl)urea].

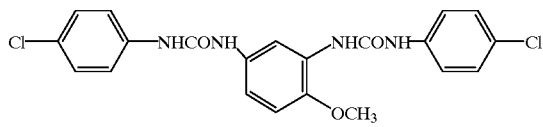

A solution of 4-chlorophenylisocyanate (1.30 g, 8.20 mmol) in dry dioxane (20 mL) is added dropwise, under N$_2$ atmosphere, to a solution of 4-methoxy-m-phenylenediaminesulfate hydrate (1.00 g, 4.23 mmol) in dry dioxane (20 mL) and in the presence of triethylamine (1.2 mL). After 72 hours of stirring at room temperature, a white precipitate appears. This precipitate is filtered and washed with H$_2$O (5×25 mL). The resulting solid is suspended in ethanol (30 mL) and stirred at room temperature for 3 hours. It is then filtered and recrystallized. The title compound is obtained as white powder. mp: >300° C.

$^1$H-NMR (DMSO-d$_6$, 200 MHz) δ: 3.85; 6.94; 7.20; 7.30–7.35; 7.50; 8.20; 8.27; 8.62; 9.49.

IR: 3297; 1638 cm$^{-1}$.

ANAL: (C$_{21}$H$_{18}$Cl$_2$N$_4$O$_3$) C: Calcd, 56.63; Found, 56.54. H: Calcd, 4.04, Found, 4.06.

N: Calcd, 12.58; Found, 12.41.

EXAMPLE 4

Preparation of N,N''-(4-methoxy-1,3-phenylene)bis [N'-(p-tolyl)urea].

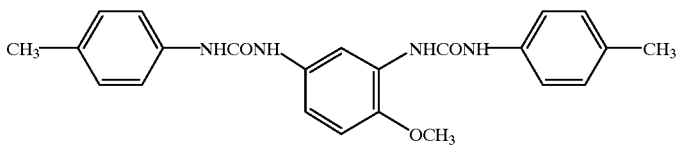

A solution of p-tolylisocyanate (1.12 g, 8.42 mmol) in dry dioxane (20 mL) is added dropwise, under N$_2$ atmosphere and with constant stirring, to a solution of 4-methoxy-m-phenylendiaminesulfate hydrate (1.00 g, 4.23 mmol) in dry dioxane (25 mL) and in the presence of triethylamine (1.2 mL). After 150 hours of stirring at room temperature, a precipitate appears. This precipitate is filtered and washed with H$_2$O (5×25 mL). The resulting solid is suspended in EtOH (30 mL) and stirred at room temperature for 4 hours. It is then filtered, washed successively with n-hexane (3×50 mL) and ethyl ether (3×50 mL), and dried. The title compound is obtained as white hygroscopic powder. mp: 162–64° C.

$^1$H-NMR (DMSO-d$_6$, 200 MHz) δ2.24; 3.84; 6.92; 7.05–7.93; 7.22; 7.33; 8.19; 8.36; 8.51; 9.24.

IR: 3296; 1640 cm$^{-1}$.

ANAL: (C$_{23}$H$_{24}$N$_4$O$_3$) C: Calcd, 68.32; Found, 67.96. H: Calcd, 5.94; Found 5.62. N: Calcd, 13.86; Found, 14.19.

EXAMPLE 5

Preparation of dimethyl N,N''-(oxydi-4,1-phenylene)bis [N'-(phenyl) carbamimidothioate]

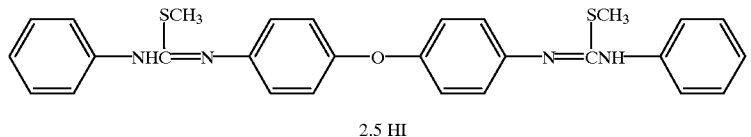

2.5 HI

A solution of iodomethane (0.9 g, 6.4 mmol) is added dropwise to a solution of N,N''-(oxydi-4,1-phenylene)bis [N'-(phenyl)thiourea] (0.5 9, 1.06 mmol) in ethanol (20 mL) at room temperature and with constant stirring. After 30 minutes of stirring at room temperature, the mixture is heated to reflux for 5 hours, observing total dissolution. The solvent is removed under reduced pressure and the resulting solid is recrystallized (EtOH), and the title compound is obtained as yellow powder. mp: 90° C.

$^1$H-NMR (DMSO-d$_6$, 200 MHz) δ: 2.62; 6.99; 7.29; 7.29–7.40; 10.00–11.00.

IR: 3200–2900; 1690–1580 cm$^{-1}$.

MS-DIP (70 eV) m/z: 402; 301; 150; 135; 77.

ANAL: (C$_{28}$H$_{26}$N$_4$OS$_2$. 2.5 HI) C: Calcd, 41.07; Found, 41.00. H: Calcd, 3.50; Found, 3.39. N: Calcd, 6.84; Found, 6.67.

EXAMPLE 6

Preparation of N,N''-(4-methoxy-1,3-phenylene)bis[N'-(4-chlorophenyl)thiourea]

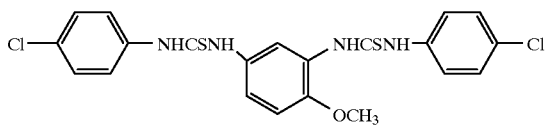

A solution of 4-chlorophenylisothiocyanate (1.43 g, 8.43 mmol) in dry dioxane (20 mL) is added dropwise, under $N_2$ atmosphere and with constant stirring, to a solution of 4-methoxy-m-phenylendiaminesulfate hydrate (1.00 g, 4.23 mmol) in dry dioxane (25 mL) and in the presence of triethylamine (1.2 mL). After 100 hours of stirring at room temperature, a precipitate appears. This precipitate is filtered and washed with $H_2O$ (5×30 mL). The resulting solid is suspended in ethanol (30 mL) and stirred at room temperature for 5 hours. It is then filtered, washed successively with n-hexane (4×20 mL) and ethyl ether (4×20 mL) and dried. The title compound is obtained as white powder. mp: 114–16° C.

$^1$H-NMR (DMSO-$d_6$, 200 MHz) δ: 3.84; 7.03; 7.23–7.36; 7.52; 8.02; 9.27.

IR: 1594 cm$^{-1}$.

ANAL: ($C_{21}H_{18}Cl_2N_4O_2S_2 \cdot H_2O$) C: Calcd, 50.91; Found, 50.85. H: Calcd. 4.04; Found, 4.03. N Calcd, 11.31; Found, 11.03.

EXAMPLE 7

Preparation of N,N''-(4-methoxy-1,3-phenylene)bis[N'-(4-nitrophenyl)thiourea]

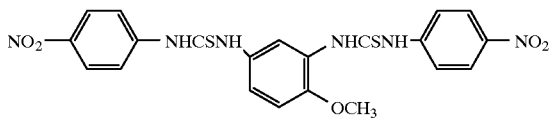

A solution of 4-nitrophenylisothiocyanate (1.52 g, 8.43 mmol) in dry dioxane (20 mL) is added dropwise, under $N_2$ atmosphere and with constant stirring, to a solution of 4-methoxy-m-phenylendiaminesulfate hydrate (1.00 g, 4.23 mmol) in dry dioxane (20 mL) and in the presence of triethylamine (1.2 mL). After 120 hours of stirring at room temperature, a yellow precipitate appears. This precipitate is filtered and washed with $H_2O$ (7×25 mL). The resulting solid is suspended in IsprOH (25 mL) and stirred at room temperature for 5 hours. It is then filtered and recrystallized. The title compound is obtained as yellow powder. mp: 190–92° C.

$^1$H-NMR (DMSO-$d_6$, 200 MHz) δ: 3.86; 7.09; 7.34; 7.81–8.01; 8.17; 9.68; 10.24–10.53.

IR: 3337; 1606 cm$^{-1}$.

ANAL: ($C_{21}H_{18}N_6O_5S_2$) C: Calcd, 50.60; Found. 50.77. H: Calcd. 3.61; Found, 3.78. N: Calcd, 16.87; Found, 16.57.

EXAMPLE 8

Preparation of dimethyl N,N''-(oxydi-4,1-phenylene)bis[N'-(4-nitrophenyl)carbamimidothioate]

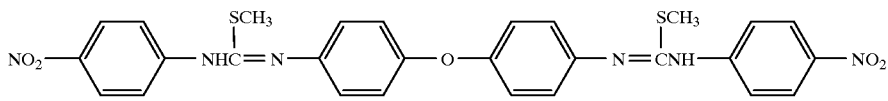

2 HI

Iodomethane (0.30 g, 2.11 mmol) is added dropwise, with stirring, to a solution of N,N''-(oxydi-4,1-phenylene)bis[N'-(4-nitrophenyl)thiourea] (0.50 g, 0.85 mmol) in ethanol (20 mL). After 2 hours of stirring at room temperature, the mixture is heated to reflux for 30 hours, observing total dissolution. This solution is treated, while hot, with active carbon and then filtered. It is concentrated partially until its volume is 10 mL. After 24 hours, a very hygroscopic yellow-orange solid appears. The title compound is obtained as yellow-orange solid. mp: 155–57° C.

$^1$H-NMR (DMSO-$d_6$, 200 MHz) δ; 2.46; 4.07–4.43; 6.59; 6.95–7.72; 7.74; 7.93; 7.15–7.24; 11.01.

IR: 3200–2900; 1595 cm$^{-1}$.

ANAL: ($C_{28}H_{24}N_6O_5S_2$) C: Calcd, 39.82; Found, 40.32. H: Calcd, 3.08; Found, 3.55. N: Calcd, 9.95; Found, 9.74.

EXAMPLE 9

Preparation of bis[N-(3-methoxyphenyl)aminosulfonyl](oxydi-4,1-phenylene)

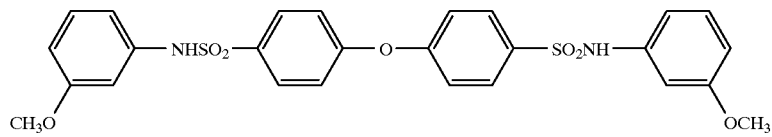

A solution of 4,4'-Bis-(chlorosulfonyl)biphenyl ether (1 g, 2.72 mmol) in dry $CH_2Cl_2$ (20 mL) is added dropwise, under N₂ atmosphere, to a mixture of m-anisidine (1.22 mL, 10.89 mmol) and pyridine (0.44 mL, 5.44 mmol), dissolved in dry CH₂Cl₂ (20 mL) and with magnetic stirring at room temperature. Stirring is maintained at room temperature for 12 days. When this time has elapsed, the solution is concentrated by rotatory evaporation and H₂O (50 mL) is added. The precipitate that forms is then isolated by vacuum filtration. This precipitate is then added to KOH 5% (40 mL). The mixture is stirred magnetically for 1 hour. Next, the mixture is filtered and HCl 35% is then added, until pH=1. The precipitate that forms is collected by vacuum filtration. The title compound is obtained as white powder. mp: 164–65° C.

¹H-NMR (DMSO-d₆, 200 MHz) δ: 3.66; 6.59–6.69; 7.10–7.21; 7.80; 10.31.

IR: 3255; 1337; 1254; 1160; 835; 754 cm⁻¹.

MS-DIP (70 eV) m/z: 540; 354; 122; 95.

ANAL: (C₂₆H₂₄N₂O₇S₂) C: Calcd, 57.77; Found, 58.07. H: Calcd, 4.44; Found, 4.59. N: Calcd, 5.18; Found, 5.03.

¹H-NMR (DMSO-d₆, 200 MHz) δ: 2.19; 6.88; 7.00; 7.68; 7.86; 8.16; 10.32.

IR: 3246; 1510; 1323; 811; 681 cm⁻¹.

MS-DIP (70 eV) m/z: 416; 246; 106.

ANAL: (C₂₀H₂₀N₂O₄S₂) C: Calcd, 57.69; Found, 57.71. H: Calcd, 4.80; Found, 4.97. N: Calcd. 6.73: Found, 6.79.

EXAMPLE 11

Preparation of bis[N-(3-methylphenyl) aminosulfonyl](oxydi-4,1-phenylene)

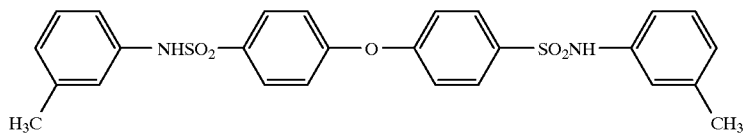

EXAMPLE 10

Preparation of N,N''-(1,3-phenylene)bis[N-(p-tolyl) aminosulfonyl]

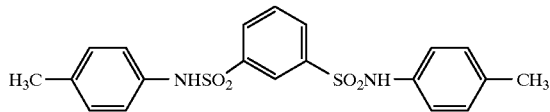

A solution of 1,3-benzendisulfonyl chloride (1 g, 363 mmol) in dry CH₂Cl₂ (20 mL) is added dropwise, under N₂ atmosphere, to a mixture of p-toluidine (1.55 g, 14.52 mmol) and pyridine (0.59 mL, 7.26 mmol), dissolved in dry CH₂Cl₂ (20 mL) and with magnetic stirring at room temperature. Stirring is maintained at room temperature for 17 days. When this time has elapsed, the solution is concentrated by rotatory evaporation and H₂O (50 mL) is added. The precipitate that forms is then isolated by vacuum filtration. This precipitate is then added to a solution of KOH 5% (50 mL). The mixture is stirred magnetically for 1 hour. Next, the mixture is filtered and HCl 35% is then added, until pH=1. The precipitate that forms is collected by vacuum filtration. The title compound is obtained as white needles. mp: 189–90° C.

A mixture of m-toluidine (1.18 mL, 10.89 mmol) and pyridine (0.44 mL, 5.44 mmol) dissolved in dry CH₂Cl₂ (20 mL) is stirred magnetically at room temperature. A solution of 4,4'-bis-(chlorosulphonyl)biphenyl ether (1 g, 2.72 mmol) dissolved in dry CH₂Cl₂ (20 mL) is slowly added dropwise under N₂ atmosphere. Stirring is maintained at room temperature for 15 days. When this time has elapsed, the solution is concentrated by rotatory evaporation and added to a solution of KOH 5% (50 mL). The mixture is stirred magnetically for 1 hour. It is then filtered and HCl 35% is added over the filtrate until pH=1. The precipitate that forms is collected by vacuum filtration and then washed with a solution saturated with HCO₂K. The title compound is obtained as beige powder. mp 68–69° C.

¹H-NMR (DMSO-d₆, 200 MHz) δ2.18; 6.81–6.90; 7.06–7.18; 7.78.

IR: 3256; 1581; 1395; 1329; 1245; 1153; 874; 782 cm⁻¹.

MS-DIP (70 eV) m/z: 508; 338; 168; 106.

ANAL: (C₂₆H₂₄N₂O₅S₂) C: Calcd, 61.42; Found, 61.29. H: Calcd, 4.72: Found, 4.70. N: Calcd, 5.51; Found, 5.47.

EXAMPLE 12

Preparation of dimethyl N,N''-(oxydi-4,1-phenylene)bis[N'-(2-phenylethyl) carbamimidothioate]

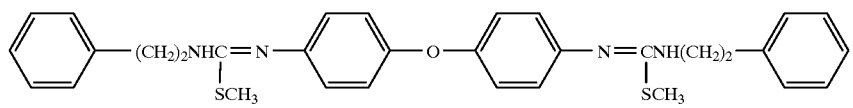

Iodomethane (0.30 g, 12.0 mmol) is added dropwise, with stirring and at room temperature, to the product of Example 15 (0.50 g) in EtOH (20 mL). The mixture is stirred at room temperature for 2 hours and then is refluxed for 5 hours. The solvent is partially eliminated. After 24 hours at room temperature, a solid appears. The title compound is obtained as cream solid. mp: 192–4° C.

$^1$H-NMR (DMSO-d$_6$, 200 MHz) δ (ppm): 2.52; 2.99; 3.71; 7.16; 7.31–7.35; 9.13 10.72.

IR (BrK) cm$^{-1}$: 3200–2900; 1600.

MS-DIP (70 eV) m/z (%): 163; 105.

Anal (C$_{32}$H$_{34}$N$_4$OS$_2$. 2HI) C: Calcd. 47.42, Found, 47.49; H: Calcd. 4.45, Found, 4.66; N: Calcd, 6.91, Found 6.67.

EXAMPLE 13

Preparation of N,N''-(methylenedi-4,1-phenylene) bis [benzenecarboximidamide]

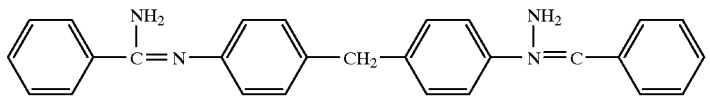

A mixture of 4,4'-diaminodiphenylmethane (1.0 g, 5.37 mmol) and methylbenzimidate hydrochloride (2.05 g, 12.0 mmol) is added slowly, at room temperature, over a stirred solution of glacial acetic acid (1.5 g, 25.0 mmol) and anhydrous sodium acetate (2.05 g, 25.0 mmol) in dioxane (50 mL). The mixture is stirred at room temperature for 48 hours and then poured over H$_2$O (200 mL) and basified with 10% NH$_4$OH (50 mL). The solid obtained is collected and purified. The title compound is obtained as a white cream solid. mp: 178–9° C.

$^1$H-NMR (DMSO-d$_6$, 200 MHz) δ (ppm): 3.86; 6.31; 6.80; 7.16; 7.43; 7.92.

IR (BrK) cm$^{-1}$: 3354; 1618.

MS-DIP (70 eV) m/z (%): 404; 300; 104.

Anal (C$_{27}$H$_{24}$N$_4$) C: Calcd. 80.19, Found, 79.90; H: Calcd. 5.94, Found, 5.98; N: Calcd, 13.86, Found, 13.96.

EXAMPLE 14
Preparation of N,N''-(oxydi-4,1-phenylene)bis [N'-(4-nitrophenyl)thiourea]

A solution of 4-nitrophenylisothiocyanate (0.90 g, 5.0 mmol) in dry dioxane (30 mL) is slowly added, under nitrogen atmosphere and with stirring, to a solution of 4,4'-diaminodiphenylether (0.50 g, 2.50 mmol) in dry dioxane (30 mL). After 24 hours of stirring at room temperature, a solid appears, which is filtered and washed with n-hexane (3×25 mL) and Et$_2$O (3×25 mL) and purified. The title compound is obtained as yellow power. mp: 156–8° C.

$^1$H-NMR (DMSO-d$_6$, 200 MHz) δ7.06; 7.53; 7.87; 8.24; 10.29; 10.40.

IR (BrK) 3323; 1495; 1331 cm$^{-1}$.

MS-DIP (70 eV) m/z: 242; 200; 180; 138.

ANAL. (C$_{26}$H$_{20}$N$_6$O$_5$S$_2$) C: Calcd. 55.71, Found, 55.97. H: Calcd. 3.57; Found, 3.56. N: Calcd, 15.00; Found, 14.69.

EXAMPLE 15

Preparation of N,N''-(oxydi-4,1-phenylene)bis[N'-(2-phenylethyl)thiourea]

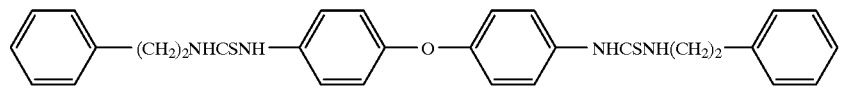

A solution of 2-phenylethylisothiocyanate (0.81 g, 5.0 mmol) in dry dioxane (20 mL) is added dropwise, under nitrogen atmosphere and with stirring, to a solution of 4,4'-diaminodiphenylether (0.50 g, 2.50 mmol) in dry dioxane (30 mL). After 36 hours of stirring at room temperature, the solvent is removed by vacuum. The residue obtained is stirred for 2 hours with a mixture of 2-propanol/n-hexane (1:1, 50 mL). The solid that precipitates is filtered and purified. The title compound is obtained as white powder. mp: 187–8° C.

$^1$H-NMR (DMSO-d$_6$, 200 MHz) δ2.87; 3.71; 6.95; 7.27–7.34; 7.66; 9.51.

IR (BrK) 3236; 1345 cm$^{-1}$.

ANAL. (C$_{30}$H$_{30}$N$_4$OS$_2$) C: Calcd. 68.44; Found 68.45. H: Calcd. 5.70; Found 5.88. N: Calcd. 10.65; Found 10.67.

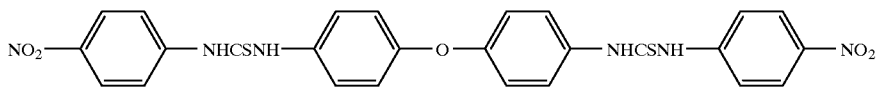

EXAMPLE 16

Preparation of N,N"-(oxydi-4,1-phenylene)bis(2-furancarboxamide)

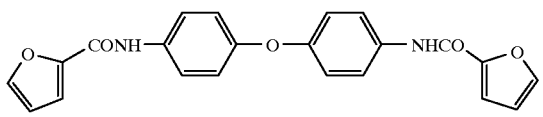

A mixture of 4,4'-diaminodiphenylether (0.65 g, 3.25 mmol) and triethylamine (0.66 g, 6.53 mmol), dissolved in dry $CH_2Cl_2$ (15 mL), is stirred magnetically at room temperature. Furan-2-carbonsaurechloride (0.65 g, 4.97 mmol) dissolved in dry $CH_2Cl_2$ (5 mL) is added dropwise to the mixture. Stirring is maintained for 2 hours at room temperature. The white precipitate obtained is isolated by vacuum filtration and then washed abundantly with $H_2O$. The title compound is obtained as white powder. mp: 181.5–182° C.

$^1$H-NMR (DMSO-$d_6$, 200 MHz) δ: 6.70; 7.01; 7.31–7.33; 7.75; 7.93; 10.22.

IR: 3273; 3129; 1656; 1274; 832 cm$^{-1}$.

MS-DIP (70 eV) m/z: 388.05; 293.15; 95.05.

ANAL: ($C_{22}H_{16}N_2O_5 \cdot ½H_2O$) C,H,N. C: Calcd, 66.50; Found, 66.51. H: Calcd, 4.28; Found, 4.16. N: Calcd, 7.05; Found, 6.87.

EXAMPLE 17

Preparation of bis(4-chlorobenzyloxy)(sulfonyldi-4,1-phenylene)

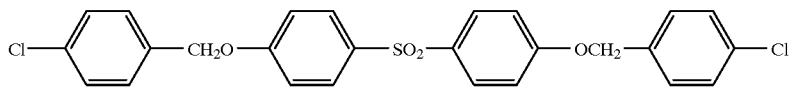

Bis(4-hydroxyphenyl)sulfon (1.0 g, 4.0 mmol) is added to a suspension of triturated KOH (2.11 g, 32 mmol) in anhydrous DMSO (30 mL), at room temperature and with magnetic stirring. Immediately afterwards, a solution of 4-chlorobenzyl chloride (2.57 g, 16 mmol) in dry anhydrous DMSO (20 mL) is added. Stirring is maintained for 24 hours. Next, the mixture is added to water (200 mL) and treated with $CH_2Cl_2$ (3×50 mL). The organic phase is washed with $H_2O$ (2×50 mL), dried over anhydrous $Na_2SO_4$ and filtered. The solvent is vacuum evaporated. The title compound is obtained as white powder. mp: 164–66° C.

$^1$H-NMR (DMSO-$d_6$, 200 MHz) δ: 518; 7.18; 7.46; 7.86.

IR: 1591; 1150; 1105 cm$^{-1}$.

MS-DIP (70 eV) m/z: 498; 125; 89.

ANAL: ($C_{26}H_{20}Cl_2O_4S$) C,H,N. C: Calcd, 62.54; Found, 62.66. H: Calcd, 4.01; Found, 4.16.

EXAMPLE 18

Preparation of bis(4-bromobenzyloxy)(sulfonyldi-4,1-phenylene)

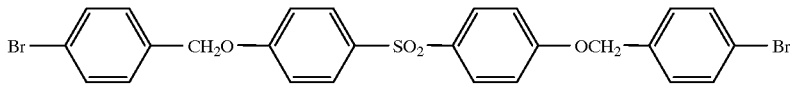

Bis(4-hydroxyphenyl)-sulfon (1.0 g, 4.0 mmol) is added to a suspension of triturated KOH (2.11 g, 32 mmol) in anhydrous DMSO (30 mL), at room temperature and with magnetic stirring. Immediately afterwards, a solution of 4-bromobenzyl bromide (4.0 g, 16 mmol) in anhydrous DMSO (20 mL) is added. Stirring is maintained for 24 hours. Next, the mixture is added to water (200 mL) and treated with $CH_2Cl_2$ (3×50 mL). The organic phase is washed with $H_2O$ (2×50 mL), dried over anhydrous $Na_2SO_4$ and filtered. The solvent is vacuum evaporated. The title compound is obtained as white solid. mp: 183–183.5° C.

$^1$H-NMR (DMSO-$d_6$, 200 MHz) δ5.19; 718; 7.39; 7.59; 7.85.

IR: 1589; 1151; 807; 556 cm$^{-1}$.

MS-DIP (70 eV) m/z: 588; 432; 171; 169.

ANAL: ($C_{26}H_{20}Br_2O_4S$) C,H,N. C: Calcd, 53.06; Found, 52.79. H: Calcd, 3.40; Found 3.42.

EXAMPLE 19

Preparation of bis [(4-pyridyl)methoxy](sulfonyldi-4,1-phenylene)

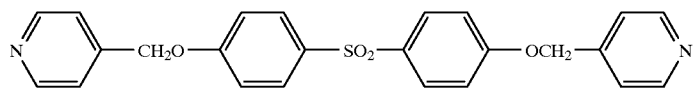

A solution of 4-(chloromethyl)pyridine hydrochloride (2.79 g, 17 mmol) in N,N-dimethylformamide (40 mL) is added dropwise to a suspension of bis-(4-hydroxyphenyl) sulfon (2.0 g, 8.0 mmol) and $K_2CO_3$ (4.72 g, 34 mmol) in N,N-dimethylformamide (40 mL), at room temperature and with magnetic stirring. Stirring is maintained for 24 hours. When this time elapses, $K_2CO_3$ (4.72 g, 34 mmol) is added and stirring is continued for another 24 hours. After this time has elapsed, the mixture is added over $H_2O$ (200 mL) and the product is taken up with AcOEt (3×100 mL). The organic phase is washed with NaOH 2N (3×100 mL), distilled $H_2O$ (3×100 mL) and HCl 2N (3×50 mL). The aqueous fractions obtained from the washings with HCl 2N are collected together and basified with NaOH 10N. The product is taken up with AcOEt (3×50 mL) and the organic phase is dried with anhydrous $Na_2SO_4$ and filtered. The solvent is vacuum dried. The solid obtained is purified by silica gel column [KIESELGEL 60] using AcOEt as the eluent. The title product is obtained as pale brown powder. mp: 182–84° C.

$^1$H-NMR (DMSO-$d_6$, 200 MHz) δ: 5.00; 6.89; 7.13–7.19; 7.74; 8.50.

IR: 3035; 2923; 1592; 1260; 1149; 815 cm$^{-1}$.

MS-DIP (70 eV) m/z: 432; 354; 184; 108; 92.

ANAL: ($C_{24}H_{20}N_2O_4S$) C,H,N. C: Calcd, 66.67; Found, 66.73. H; Calcd, 4.63; Found, 4.87. N: Calcd, 6.48; Found, 6.41.

EXAMPLE 20

Preparation of bis(4-fluorobenzyloxy)(sulfonyldi-4, 1-phenylene)

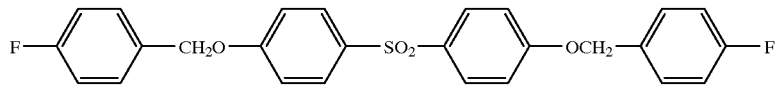

Bis(4-hydroxyphenyl)sulfon (10 g, 4.0 mmol) is added to a suspension of triturated KOH (2.11 g, 32 mmol) in anhydrous DMSO (30 mL), at room temperature and with magnetic stirring. Immediately afterwards, a solution of 4-fluorobenzyl chloride (2.31 g, 16 mmol) in anhydrous DMSO (20 mL) is added. The mixture is stirred for 24 hours. Next, the mixture is poured over $H_2O$ (200 mL) and taken up with $CH_2Cl_2$ (3×50 mL). The organic phase is washed with $H_2O$ (2×50 mL), dried with anhydrous $Na_2SO_4$, and filtered. The solvent is evaporated until dry. The title product is obtained as white powder. mp: 177–177.5° C.

$^1$H-NMR ($Cl_3CD$, 200 MHz) δ: 5.04; 7.01; 7.10; 7.37; 7.85.

IR 1593; 1250; 1151; 830 cm$^{-1}$.

MS-DIP (70 eV) m/z: 466; 358; 250; 109.

ANAL: ($C_{26}H_{20}F_2O_4S$) C,H,N. C: Calcd, 66.95; Found, 66.99. H: Calcd, 4.29; Found, 4.46. N: Calcd, 0.00; Found, 0.05.

EXAMPLE 21

Preparation of hydroxy(4-nitrobenzyloxy) (sulfonyldi-4,1-phenylene)

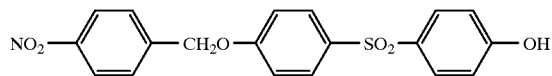

4-Nitrobenzylbromide (1.37 g, 8.5 mmol) is added to a suspension of bis-(4-hydroxyphenyl)sulfon (1.0 g, 4.0 mmol) and triethylamine (0.6 mL, 4.25 mmol) in dry diox-ane (25 mL). The mixture is refluxed for 10 hours. After the time elapses, the mixture is left to cool and a dense orange colored oil is obtained. The mixture is poured over distilled $H_2O$ (200 mL) and extracted with $CH_2Cl_2$ (3×50 mL). The organic phase obtained is washed with distilled $H_2O$ (3×50 mL), dried with anhydrous $Na_2SO_4$, and filtered. The solvent is evaporated until dry, and the solid obtained is purified in a silica gel [KIESEL GEL 60] chromatography column using a mixture of toluene/AcOEt (3:1) as the eluent. The title product is obtained as white solid. mp: 203.5–204° C.

$^1$H-NMR (DMSO-$d_6$, 200 MHz) δ5.37; 691; 7.20; 7.69–7.76; 7.84; 8.26; 10.59.

IR: 3332; 1590; 1521; 1345; 1256; 842 cm$^{-1}$.

MS-DIP (70 eV) m/z: 385; 152; 136; 70.

ANAL: ($C_{19}H_{15}NO_6S$) C,H,N. C: Calcd, 59.22; Found, 59.17. H: Calcd, 3 90; Found, 3.87. N Calcd, 3.64; Found, 3.52.

EXAMPLE 22

Preparation of (4-chlorobenzyloxy)hydroxy (sulfonyldi-4,1-phenylene)

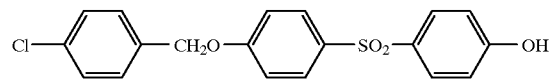

A solution of 4-chlorobenzyl chloride (1.37 g, 8.5 mmol) is added to a suspension of Bis-(4-hydroxyphenyl)sulfon (2.0 g, 8.0 mmol) and triethylamine (1.2 mL, 8.5 mmol) in dry dioxane (40 mL). The mixture is refluxed for 10 hours. After this time has elapsed, the mixture is left to cool and a dense orange colored oil is obtained. The mixture is poured over distilled $H_2O$ (200 mL) and treated with $CH_2Cl_2$ (3×50 mL) The organic phase obtained is washed with NaOH 2N (3×50 mL). Later, the aqueous extracts are joined together and neutralized with HCl (2N) The precipitate obtained is isolated by vacuum filtration and purified in a silica gel [KIESEL GEL 60] chromatography column using a mixture of toluene/AcOEt (3:1) as the eluent. The title product is obtained as white powder. mp: 146–47° C.

$^1$H-NMR (DMSO-$d_6$, 200 MHz) δ: 5.18; 6.91; 7.17; 7.44–7.46; 7.73; 7.82; 10.58.

IR: 3411; 1589; 1249; 836; 569 cm$^{-1}$.

MS-DIP (70 eV) m/z: 374; 141; 125.

ANAL: ($C_{19}H_{15}Cl_2O_4S$) C,H,N. C: Calcd, 60.89; Found, 61.35. H: Calcd, 4.01; Found 4.16.

EXAMPLE 23
Preparation of N,N''-(methylenedi-4,1-phenylene) bis[N'-(4-nitrophenyl)thiourea]

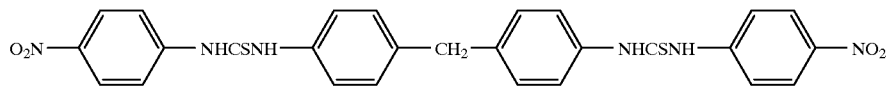

A solution of 4-nitrophenyl isothiocyanate (0.45 g, 2.52 mmol) in dioxane (25 mL) is slowly added, with magnetic stirring, to a solution of 4,4'-diaminodiphenyl methane (0.25 g, 1.26 mmol) in dioxane (10 mL). After 24 hours of stirring at room temperature, the solvent is removed by vacuum evaporation. The solid obtained is washed with n-hexane (3×25 mL) and isopropanol (3×10 mL). Next, the solid is dissolved in ethyl acetate (50 mL) and washed with water (3×25 mL). The organic phase is dried with sodium sulfate. The solvent is removed by vacuum evaporation. The titled compound is obtained as a yellow powder. mp: 115° C.

$^1$H-NMR (DMSO-$d_6$) d 3.90; 7.24; 7.39; 7.82; 8.19; 10.22; 10.34.

IR: 3410; 1500; 1327 cm$^1$.

MS-DIP (70 eV) m/z: 180.05

ANAL: ($C_{27}H_{22}N_6O_4S_2$) C,H,N. C: Calcd, 58.06; Found, 58.06. H: Calcd, 3.94; Found, 4.15. N: Calcd, 15.05; Found, 14.71.

SCHEME 1A

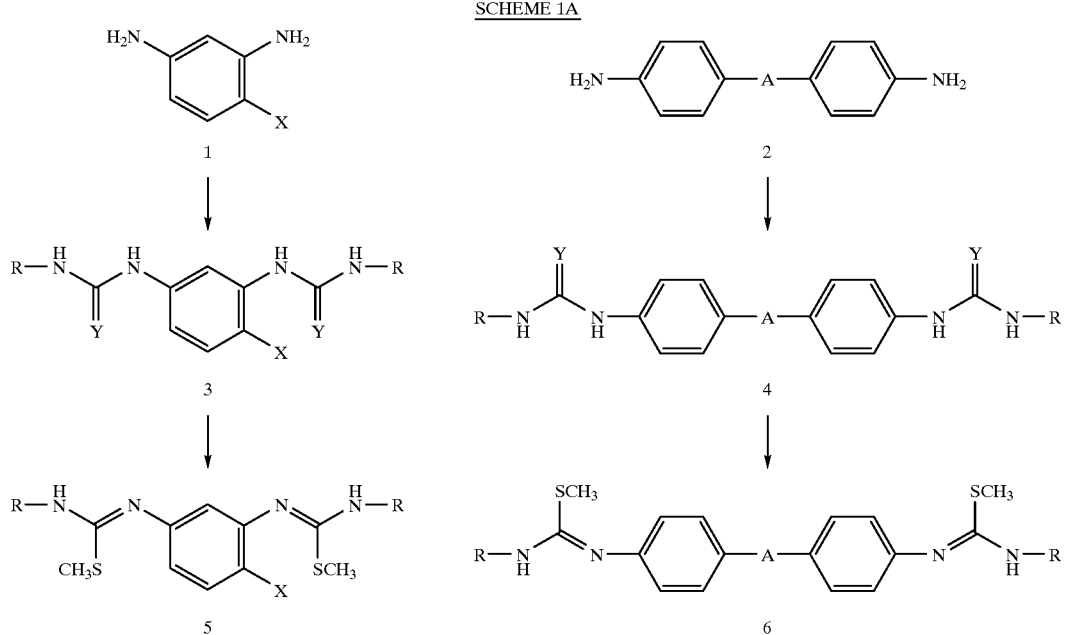

SCHEME 1B

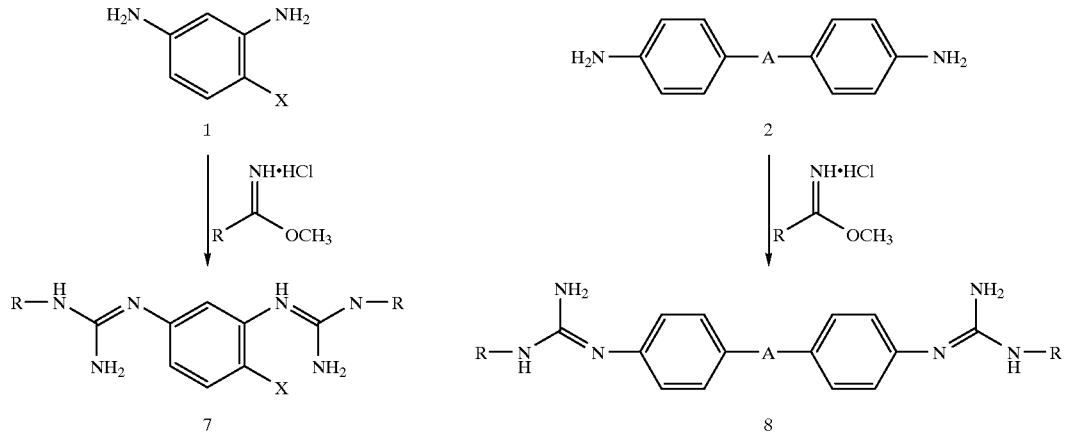

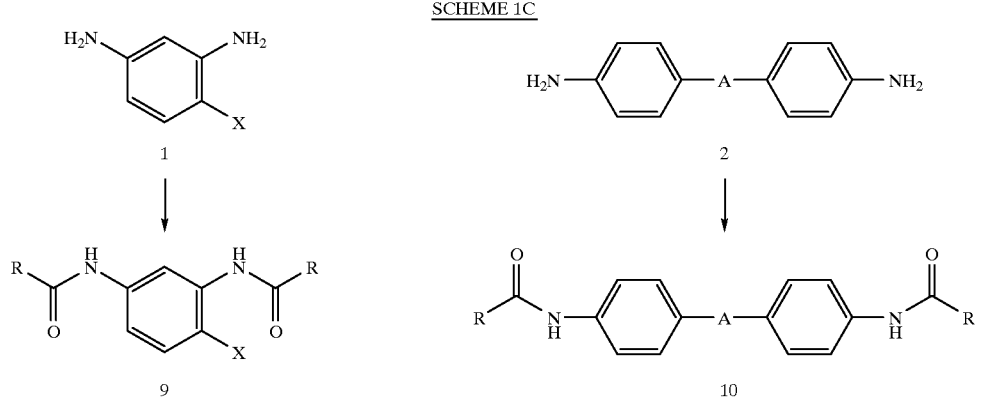
SCHEME 1C
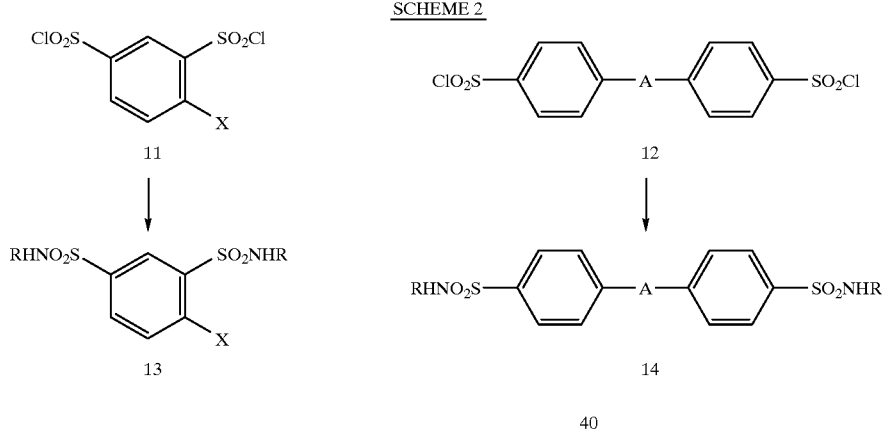
SCHEME 2
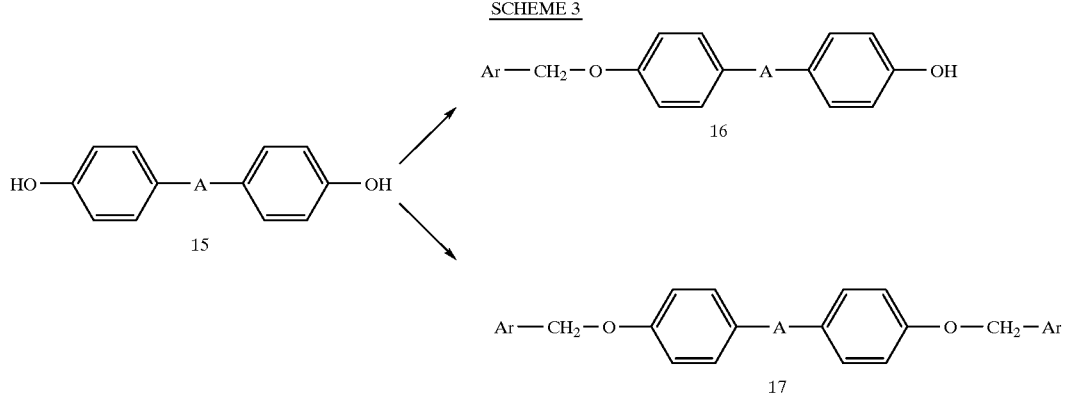
SCHEME 3

We claim:

1. A compound of formula I

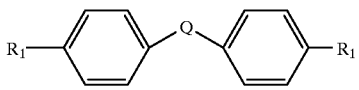

or pharmaceutically acceptable salts thereof wherein:
Q is
  (a) —O—, or
  (b) —CH$_2$—;
R$_1$ is
  (a) —N=C(SCH$_3$)(NH-phenyl),
  (b) —N=C(SCH$_3$)(NHCH$_2$CH$_2$-phenyl),
  (c) —N=C(SCH$_3$)(NH-4-nitrophenyl),
  (d) —N=C(SCH$_2$CH$_3$)(NHCH$_2$CH$_2$-phenyl),
  (e) —SO$_2$NH(3-methoxyphenyl),
  (f) —SO$_2$NH(3-methylphenyl), or
  (g) —N=C(NH$_2$)(phenyl); with the following provisos:
  (a) where Q is —O—, R$_1$ and R$_2$ are other than (g), and
  (b) where Q is —CH$_2$—, R$_1$ and R$_2$ are other than (a)–(f).

2. A compound of formula 1 according to claim 1 which is
  a) Dimethyl N,N"-(oxydi-4,1-phenylene)bis[N'-(phenyl)carbamimidothioate],
  b) Dimethyl N,N"-(oxydi-4,1-phenylene)bis[N'-(2-phenylethyl) carbamimidothioate],
  c) Dimethyl N,N"-(oxydi-4,1-phenylene)bis [N'-(4-nitrophenyl) carbamimidothioate],
  d) Diethyl N,N"-(oxydi-4,1-phenylene)bis[N'-(2-phenylethyl)carbamimidothioate],
  e) Bis[N-(3-methoxyphenyl)aminosulfonyl](oxydi-4,1-phenylene),
  f) Bis[N-(3-methylphenyl)aminosulfonyl](oxydi-4,1-phenylene), or
  g) N,N"-(Methylenedi-4,1-phenylene)bis[benzenecarboximidamide].

3. A method for treating herpes virus infection in patients which comprises topically administering to the herpetic lesion on the skin of said patients an effective amount of a compound of formula III

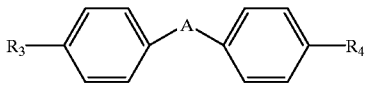

or pharmaceutically acceptable salts thereof wherein:
A is
  (a) —O—,
  (b) —CH$_2$, or
  (c) —S(=O)$_2$—;
R$_3$ and R$_4$ are the same and are
  (a) —N=C(SCH$_3$)(NH-phenyl),
  (b) —N=C(SCH$_3$)(NHCH$_2$CH$_2$-phenyl),
  (c) —N=C(SCH$_3$)(NH-4-nitrophenyl),
  (d) —N=C(SCH$_2$CH$_3$)(NHCH$_2$CH$_2$-phenyl),
  (e) —SO$_2$NH(3-methoxyphenyl),
  (f) —SO$_2$NH(3-methylphenyl),
  (g) —N=C(NH$_2$)(phenyl),
  (x) —NHC(=O)(2-furyl),
  (i) —NHC(=S)NHCH$_2$CH$_2$-phenyl,
  (j) —NHC(=S)NH(4-nitrophenyl),
  (k) —OCH$_2$(4-bromophenyl),
  (l) —OCH$_2$(4-chlorophenyl),
  (m) —OCH$_2$(4-fluorophenyl),
  (n) —OCH$_2$(4-pyridyl),
R$_3$ and R$_4$ are different and are
  (o) —OH,
  (p) —OCH$_2$(4-chlorophenyl), or
  (q) —OCH$_2$(4-nitrophenyl); with the following provisos:
  (a) where A is —O—, R$_3$ and R$_4$ are other than (k)–(q),
  (b) where A is —CH$_2$—, R3 and R$_4$ are (g) or (j), and
  (c) where A is —S(=O)$_2$—, R$_3$ and R$_4$ are other than (a)–(j).

4. A method for treating herpes virus according to claim 3, wherein the compound of formula III is
  a) Dimethyl N,N"-(oxydi-4,1-phenylene)bis[N'-(phenyl) carbamimidothioate],
  b) Dimethyl N,N"-(oxydi-4,1-phenylene)bis[N'-(2-phenylethyl) carbamimidothioate],
  c) Dimethyl N,N"-(oxydi-4,1-phenylene)bis[N'-(4-nitrophenyl) carbamimidothioate],
  d) Diethyl N,N"-(oxydi-4,1-phenylene)bis [N'-(2-phenylethyl)carbamimidothioate],
  e) Bis[N-(3-methoxyphenyl)aminosulfonyl](oxydi-4,1-phenylene),
  f) Bis[N-(3-methylphenyl)aminosulfonyl](oxydi-4,1-phenylene),
  g) N,N"-(Methylenedi-4,1-phenylene)bis[benzenecarboximidamide],
  h) N,N"-(Oxydi-4,1-phenylene)bis(2-furancarboxamide),
  i) N,N"-(Oxydi-4,1-phenylene)bis[N'-(2-phenylethyl) thiourea],
  j) N,N"-(Oxydi-4,1-phenylene)bis [N'-(4-nitrophenyl) thiourea],
  k) N,N"-(Methylenedi-4,1-phenylene)bis [N'-(4-nitrophenyl)thiourea],
  l) Bis(4-bromobenzyloxy)(sulfonyldi-4,1-phenylene),
  m) Bis(4-chlorobenzyloxy)(sulfonyldi-4,1-phenylene),
  n) Bis(4-fluorobenzyloxy)(sulfonyldi-4,1-phenylene),
  o) Bis[(4-pyridyl)methoxy](sulfonyldi-4,1-phenylene),
  p) (4-Chlorobenzyloxy)hydroxy(sulfonyldi-4,1-phenylene), or
  q) Hydroxy(4-nitrobenzyloxy)(sulfonyldi-4,1-phenylene).

5. The method of claim 3 wherein the herpes virus infection is herpes simplex type-1.

6. The method of claim 3 wherein the herpes virus infection is herpes simplex type-2.

7. The method of claim 3 wherein the herpes virus infection is varicella zoster virus.

8. The method of claim 3 wherein the effective amount is administered topically in a pharmaceutical composition.

9. A pharmaceutical composition for treating herpes viral infections in patients which comprises a compound of formula I according to claim 1 and a pharmaceutically acceptable carrier.

10. The pharmaceutical composition of claim 9 wherein said compound of formula I is present in an amount of about 0.05% to about 25% by weight.

11. The pharmaceutical composition of claim 9 wherein said compound of formula I is present in an amount of about 0.1% to about 10% by weight.

* * * * *